(12) United States Patent
Starnes

(10) Patent No.: US 10,653,423 B2
(45) Date of Patent: May 19, 2020

(54) CATHETERS FOR EMERGENCY ENDOVASCULAR SURGERY AND ASSOCIATED DEVICES, SYSTEMS, AND METHODS

(71) Applicant: University of Washington through its Center for Commercialization, Seattle, WA (US)

(72) Inventor: Benjamin W. Starnes, Seattle, WA (US)

(73) Assignee: University of Washington, Seattle, WA (US)

(*) Notice: Subject to any disclaimer, the term of this patent is extended or adjusted under 35 U.S.C. 154(b) by 1222 days.

(21) Appl. No.: 14/409,426

(22) PCT Filed: Oct. 22, 2012

(86) PCT No.: PCT/US2012/061382
§ 371 (c)(1),
(2) Date: Dec. 18, 2014

(87) PCT Pub. No.: WO2014/003809
PCT Pub. Date: Jan. 3, 2014

(65) Prior Publication Data
US 2015/0201944 A1 Jul. 23, 2015

Related U.S. Application Data

(60) Provisional application No. 61/666,548, filed on Jun. 29, 2012.

(51) Int. Cl.
*A61B 17/12* (2006.01)
*A61B 5/06* (2006.01)
(Continued)

(52) U.S. Cl.
CPC .......... *A61B 17/1204* (2013.01); *A61B 5/061* (2013.01); *A61B 17/12136* (2013.01);
(Continued)

(58) Field of Classification Search
CPC .......... A61M 17/1204; A61M 25/0068; A61M 2025/0681; A61B 17/12136
See application file for complete search history.

(56) References Cited

U.S. PATENT DOCUMENTS 3,833,003 A 9/1974 Taricco
5,188,602 A * 2/1993 Nichols .................. A61F 7/123
604/107

(Continued)

FOREIGN PATENT DOCUMENTS

WO 2002102456 A1 12/2002
WO 2011036850 A1 3/2011

OTHER PUBLICATIONS

International Search Report dated Mar. 3, 2014 in International Application No. PCT/US2012/061382, 12 pages.
(Continued)

*Primary Examiner* — Nathan R Price
*Assistant Examiner* — Melissa A Snyder
(74) *Attorney, Agent, or Firm* — Perkins Coie LLP

(57) ABSTRACT

Catheter systems configured for emergency blood-vessel occlusion and associated devices, systems, and methods are disclosed herein. A catheter system configured in accordance with a particular embodiment includes a catheter, a sheath, and an extracorporeal proximity sensor. The catheter includes an elongated body having a tip, a sealing portion, and a main shaft proximal to the sealing portion. The tip is configured to dilate a blood vessel ahead of the distal end
(Continued)

portion of the sheath as the catheter and the sheath are advanced together through the blood vessel. The distal end portion of the sheath is configured to fit snugly around the sealing portion. The catheter further includes a balloon and a proximity-sensor target less than about 10 centimeters from the balloon. The proximity sensor is configured to receive a signal from the proximity-sensor target to aid in positioning the balloon without fluoroscopic guidance.

18 Claims, 8 Drawing Sheets

(51) Int. Cl.
*A61M 25/00* (2006.01)
*A61M 25/01* (2006.01)
*A61M 29/00* (2006.01)
*A61M 25/06* (2006.01)
*A61B 90/00* (2016.01)

(52) U.S. Cl.
CPC .. *A61B 2090/3954* (2016.02); *A61M 25/0068* (2013.01); *A61M 25/0127* (2013.01); *A61M 29/00* (2013.01); *A61M 2025/0681* (2013.01)

(56) References Cited

U.S. PATENT DOCUMENTS

| | | | |
|---|---|---|---|
| 5,626,601 A | | 5/1997 | Gershony et al. |
| 6,190,393 B1* | | 2/2001 | Bevier ............... A61F 2/958 |
| | | | 604/96.01 |
| 6,319,242 B1* | | 11/2001 | Patterson ........... A61B 17/3207 |
| | | | 604/508 |
| 7,276,905 B2 | | 10/2007 | Tamaroff et al. |
| 2001/0001114 A1 | | 5/2001 | Tsugita et al. |
| 2002/0042625 A1 | | 4/2002 | Stack et al. |
| 2002/0099405 A1 | | 7/2002 | Yurek et al. |
| 2003/0135266 A1* | | 7/2003 | Chew .................. A61F 2/91 |
| | | | 623/1.16 |
| 2006/0004399 A1* | | 1/2006 | van Ockenburg .. A61M 25/001 |
| | | | 606/192 |
| 2006/0271151 A1 | | 11/2006 | McGarry et al. |
| 2010/0217189 A1* | | 8/2010 | Pepper ............. A61M 25/0075 |
| | | | 604/99.04 |
| 2010/0234838 A1 | | 9/2010 | Watson |
| 2011/0118546 A1 | | 5/2011 | Dillon |

OTHER PUBLICATIONS

European Search Report dated May 11, 2016 in European Application No. 12879782.6, 11 pages.

* cited by examiner

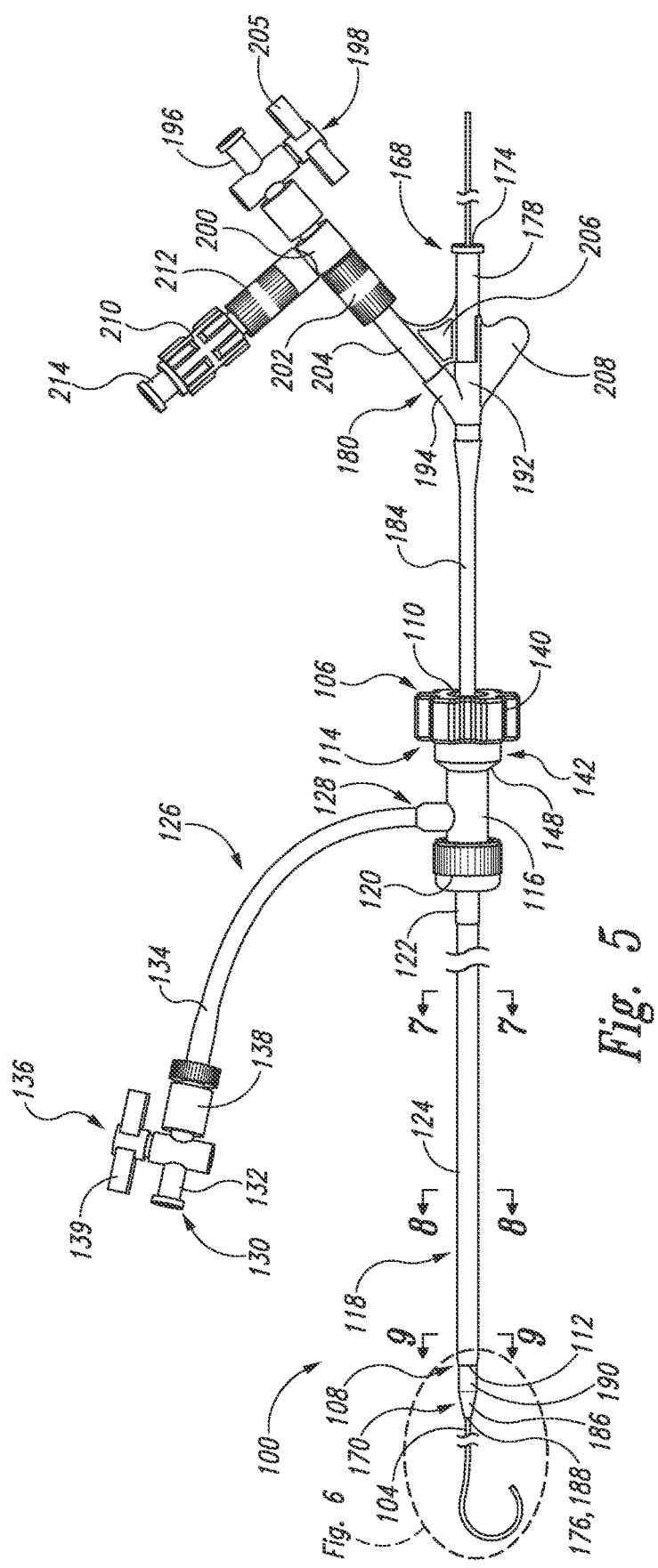
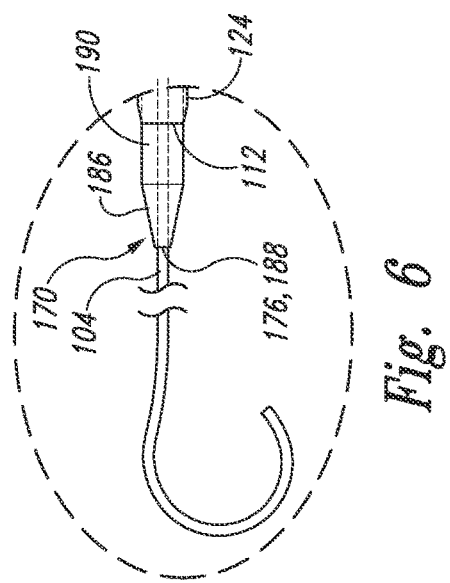

CATHETERS FOR EMERGENCY ENDOVASCULAR SURGERY AND ASSOCIATED DEVICES, SYSTEMS, AND METHODS

CROSS-REFERENCE TO RELATED APPLICATION

This claims the benefit of U.S. Provisional Patent Application No. 61/666,548, filed Jun. 29, 2012, which is incorporated herein by reference in its entirety.

TECHNICAL FIELD

The present technology is related to endovascular surgery. Some embodiments, for example, are directed to catheters, catheter systems, and methods for occluding blood vessels useful in the context of endovascular surgery.

BACKGROUND

Internal bleeding from major blood vessels can cause death within minutes or hours. Vascular trauma associated with accidents and violence (e.g., falls, automobile accidents, gunshots, etc.) and ruptured aneurysms are the most common causes of internal bleeding. For example, in the United States, about 15,000 people die annually from internal bleeding following ruptured abdominal aortic aneurysms alone, and thousands more die from internal bleeding following other types of vascular trauma. Unfortunately, mortality rates for most types of internal bleeding from major blood vessels are currently greater than 50% and have shown little or no improvement over the last several decades. Considering these relatively high rates of occurrence and mortality, innovative treatments for internal bleeding have the potential save thousands of lives annually.

Some conventional approaches to treating internal bleeding include temporarily occluding injured blood vessels upstream from vascular injuries and then repairing the blood vessels prior to reestablishing blood flow. These approaches, however, typically require either large surgical incisions for open surgery or fluoroscopic guidance for endovascular surgery, both of which are usually possible only in hospital operating rooms and trauma centers. Since the window for successfully treating internal bleeding is often very short (e.g. less than one or two hours in some cases), many patients die before they can be transported to a suitable location for treatment.

When a patient is able to reach a suitable location in time, the attending clinician typically must decide whether to perform open surgery or endovascular surgery based on the circumstances. Open surgery can have more serious complications than endovascular surgery. Conventional endovascular surgery, however, typically is slower and more challenging to execute reliably than open surgery. For example, conventional endovascular surgery typically makes use of catheters and other devices designed primarily for non-emergency use. These devices typically have intricate operational protocols poorly suited for emergencies. For these and other reasons, there is a public health need for innovation in the field of emergency endovascular surgery, such as innovation with regard to techniques and devices that facilitate more rapid and/or simplified occlusion of major blood vessels prior to vascular repair than are typically achievable using conventional techniques and devices.

BRIEF DESCRIPTION OF THE DRAWINGS

Many aspects of the present technology can be better understood with reference to the following drawings. The relative dimensions in the drawings may be to scale with respect to some embodiments. With respect to other embodiments, the drawings may not be to scale. For ease of reference, throughout this disclosure identical reference numbers may be used to identify identical or at least generally similar or analogous components or features.

FIG. 5 is a side view illustrating the sheath, the catheter, and the guide wire shown in FIG. 1 in a cooperative arrangement.

FIG. 6 is an enlarged view of a portion of FIG. 5.

DETAILED DESCRIPTION

Figure 1:
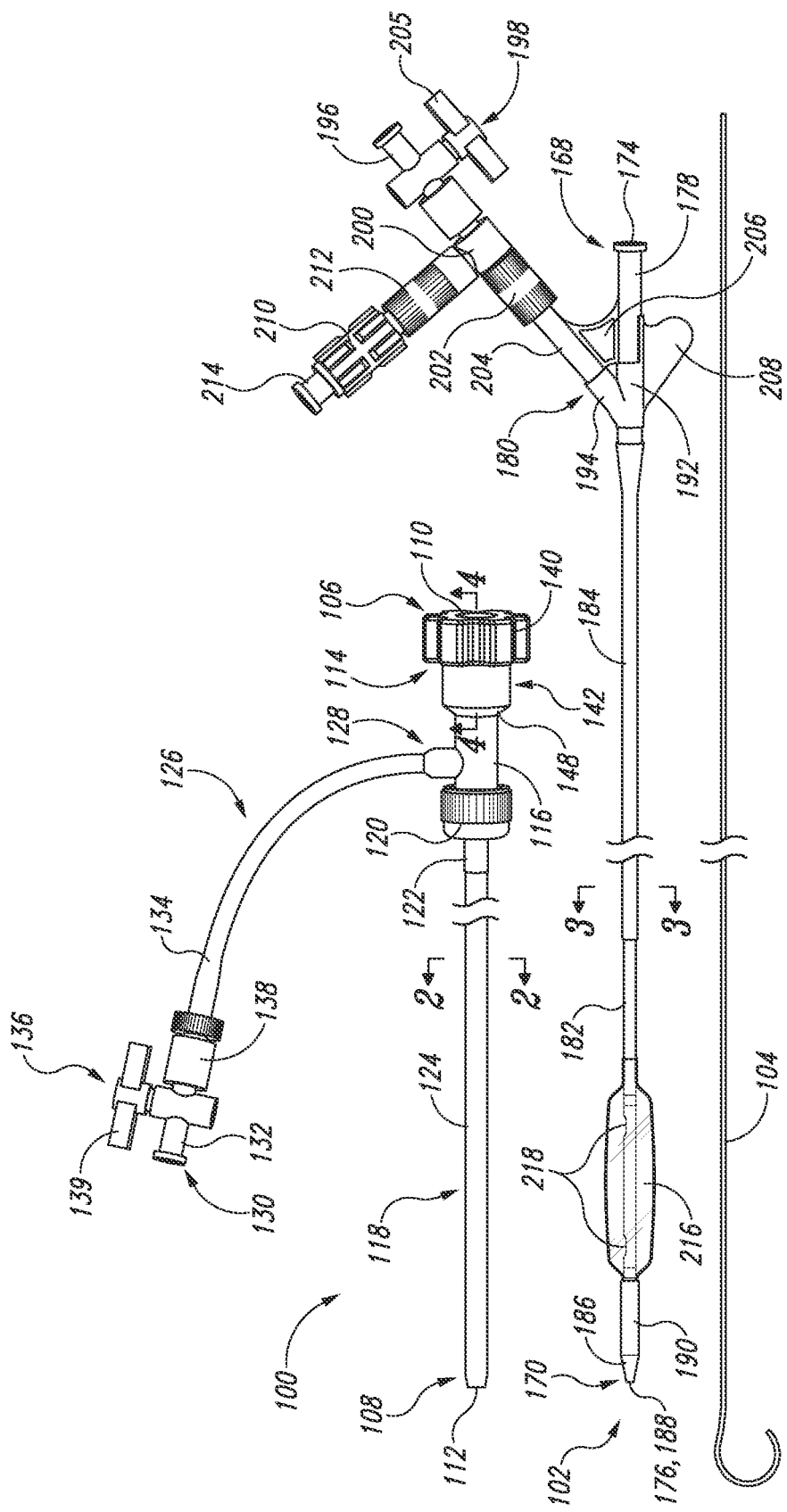
FIG. 1 is a side view illustrating a sheath, a catheter, and a guide wire configured in accordance with an embodiment of the present technology separate from one another and with the catheter in a deployed state in which a balloon of the catheter is inflated.

Specific details of several embodiments of the present technology are described herein with reference to FIGS. 1-14. Although many of the embodiments are described herein with respect to devices, systems, and methods for treating internal bleeding associated with ruptured aneurysms or other vascular trauma to the abdominal aorta, other applications and other embodiments in addition to those described herein are within the scope of the present technology. For example, some embodiments may be useful for treating internal bleeding associated with ruptured aneurysms or other vascular trauma at locations other than the abdominal aorta. Additionally, some embodiments may be useful for non-emergency endovascular surgery, e.g., vascular repair before aneurysm rupture. It should be noted that some embodiments of the present technology can have different configurations, components, or procedures than those shown or described herein. Moreover, a person of ordinary skill in the art will understand that some embodiments of the present technology can have components and/or procedures in addition to those shown or described herein and that these and other embodiments can be without several of the components and/or procedures shown or described herein without deviating from the present technology.

Conventional endovascular surgery for treating ruptured abdominal aortic aneurysms typically includes inserting a needle into a femoral artery, and advancing a guide wire through the needle and along a catheterization path to the aorta, e.g., via the femoral artery, an external iliac artery, and a common iliac artery. A dilator and a sheath are then advanced together over the guide wire until a distal end of the sheath is suitably positioned within the aorta. The dilator typically has a tapered tip that gently stretches the blood vessel walls ahead of the sheath. During this process, the blood vessel walls exert a force against the tip of the dilator. Portions of the dilator proximal to the tip typically have sufficiently column strength to resist this force, e.g. to support the tip without buckling. Once the sheath is in position, the dilator is removed and a catheter is advanced through the sheath. Since the sheath holds the blood vessels along the catheterization path open while the catheter is advanced, the column strength of the catheter can be less than that of the dilator. Conventional catheters, for example, typically are thin walled to favor greater internal diameter rather than greater column strength. In many cases, conventional catheters include radiopaque markers that facilitate fluoroscopic positioning prior to aortic occlusion.

Catheters configured in accordance with some embodiments of the present technology have one or more features that enhance their usefulness for emergency endovascular surgery. For example, in some embodiments, the catheters are configured for faster and/or less complex operation than conventional catheters typically used for blood-vessel occlusion. Although removing a dilator and advancing a conventional catheter in its place may in some cases (e.g., non-emergencies) have few drawbacks, in the context of emergency endovascular surgery these steps are often problematic. In some embodiments, the need for these steps can be reduced or eliminated, which can lead to faster blood-vessel occlusion and better outcomes. For example, a catheter configured in accordance with an embodiment of the present technology can have a tapered tip and sufficient column strength to be advanced through blood vessels along a catheterization path together with an associated sheath. In this way, the catheter can act as a dilator. Furthermore, the catheter can include a balloon for blood-vessel occlusion and a pressure-relief valve that opens before a pressure within the balloon reaches a level that could damage the blood vessel being occluded. This can allow a clinician to increase the pressure within the balloon aggressively so that the pressure rapidly reaches a suitable level for occlusion. In some embodiments, the catheter can be configured for use with or without fluoroscopic guidance. This can allow the catheter to be positioned more rapidly than would be possible using fluoroscopic guidance in conventional settings, e.g., hospital operating rooms and trauma centers. Furthermore, in some cases, the catheter can be suitable for use in unconventional settings, e.g., in ambulances, at the scenes of accidents, on battlefields, etc.

Figure 2:
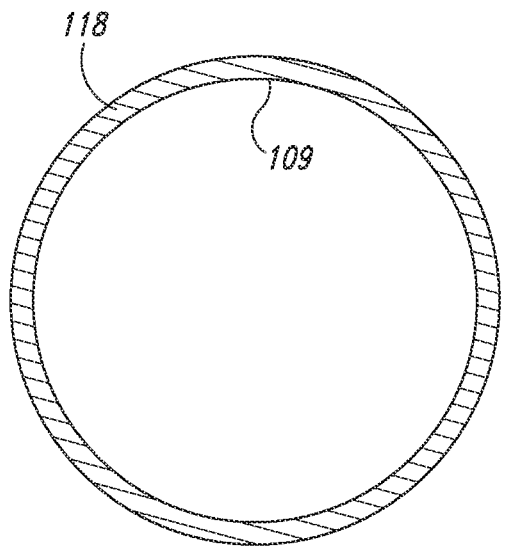
FIGS. 2 and 3 are cross-sectional end views taken, respectively, along lines 2-2 and 3-3 in FIG. 1.
Figure 3:
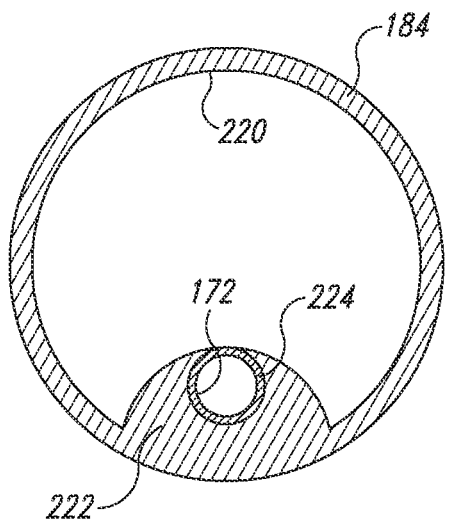

FIG. 1 is a side view illustrating a sheath 100, a catheter 102, and a guide wire 104 configured in accordance with an embodiment of the present technology. FIGS. 2 and 3 are cross-sectional end views taken, respectively, along lines 2-2 and 3-3 in FIG. 1. With reference to FIGS. 1-3 together, the sheath 100 can include a proximal end portion 106, a distal end portion 108, and a central lumen 109 having a first opening 110 at the proximal end portion 106 and a second opening 112 at the distal end portion 108. The central lumen 109 can extend axially from the first opening 110 to the second opening 112. The catheter 102 can be slidingly received within the central lumen 109 such that one portion of the catheter 102 extends beyond the first opening 110 and another portion of the catheter 102 extends beyond the second opening 112. The axial length of the sheath 100 from the first opening 110 to the second opening 112 can be from about 40 centimeters to about 90 centimeters, from about 40 centimeters to about 70 centimeters, from about 40 centimeters to about 60 centimeters, or within another suitable range. For example, the axial length of the sheath 100 from the first opening 110 to the second opening 112 can be about 50 centimeters.

In some embodiments, the sheath 100 includes an adjustable compression seal 114 toward the proximal end portion 106. Distal to the compression seal 114, the sheath 100 can include a first tee fitting 116, an elongated tube 118, and a first transition fitting 120 therebetween. The tube 118 can include a reinforced proximal end portion 122 toward the first transition fitting 120 and a main portion 124 distal to the proximal end portion 122. The sheath 100 can have a wall thickness that is generally consistent along the main portion 124 and decreases gradually at the distal end portion 108 such that the distal end portion 108 tapers inwardly toward the second opening 112. In some embodiments, the sheath 100 can be reinforced to resist collapsing in response to circumferential compression or other forces acting laterally against the main portion 124. For example, the sheath 100 can include a reinforcing member (not shown) (e.g., a braided metal tube) embedded within the main portion 124. Furthermore, the sheath 100 can have a hydrophilic coating (not shown) on its outer surface to facilitate movement through relatively small blood vessels. In some embodiments, the sheath 100 is a FLEXOR, sheath available from Cook Group Incorporated (Bloomington, Ind.).

Extending laterally from the first tee fitting 116, the sheath 100 can include a valve assembly 126 having a first end portion 128 positioned at the first tee fitting 116 and a second end portion 130 positioned opposite to the first end portion 128. The valve assembly 126 can include an aspirating port 132 toward the second end portion 130 and an aspirating conduit 134 toward the first end portion 128. Between the aspirating port 132 and the aspirating conduit 134, the valve assembly 126 can include a aspirating valve 136 and a second transition fitting 138, with the aspirating valve 136 adjacent to the aspirating port 132 and the second transition fitting 138 between the aspirating valve 136 and the aspirating conduit 134. The aspirating valve 136 can include a first thumb turn 139 that can be rotated 90° to open or close the valve assembly 126. For example, the first thumb turn 139 can be generally aligned with the length of the aspirating port 132 when the aspirating valve 136 is open and generally perpendicular to the aspirating port 132 when the aspirating valve 136 is closed.

Figure 4:
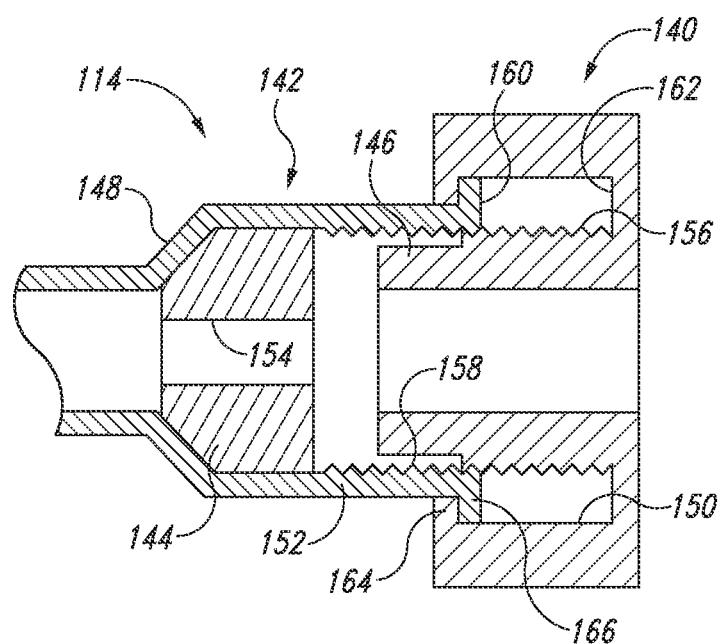
FIG. 4 is a partially cross-sectional side view taken along line 4-4 in FIG. 1.

FIG. 4 is a partially cross-sectional side view taken along line 4-4 in FIG. 1. With reference to FIG. 4, the compression seal 114 can include a locking nut 140, a housing 142, and a resilient member 144 between a stem portion 146 of the locking nut 140 and a seat portion 148 of the housing 142. The locking nut 140 can include an annular groove 150 configured to receive a cylindrical portion 152 of the housing 142. The resilient member 144 can include a coaxial bore 154 sized to receive the catheter 102 loosely or at a relatively low level of compression. Rotating the locking nut 140 relative to the housing 142 can tighten the compression seal 114. For example, the locking nut 140 can include a plurality of male threads 156 positioned within the groove 150, and the housing 142 can include a cooperating plurality of female threads 158 positioned within the cylindrical portion 152. When the locking nut 140 is rotated in one direction relative to the housing 142, the cylindrical portion 152 can move into the groove 150 such that the stem portion 146 presses the resilient member 144 against the seat portion 148. When the locking nut 140 is rotated in an opposite direction relative to the housing 142, the cylindrical portion 152 can move out of the groove 150 to cause the stem portion 146 to release the resilient member 144.

The resilient member 144 can be at least partially tapered such that the resilient member 144 wedges into the seat portion 148 when the stem portion 146 presses the resilient member 144 against the seat portion 148. A portion of the force from the seat portion 148 can act inwardly against the resilient member 144 to cause the diameter of bore 154 to resiliently decrease and/or to cause the resilient member 144 to resiliently deform and press against the catheter 102 when the catheter 102 is positioned within the bore 154. Friction between the resilient member 144 and the catheter 102 can increase the force necessary to move the catheter 102 longitudinally relative to the sheath 100. When the compression seal 114 is fully tightened, a proximal end 160 of the housing 142 can press against a proximal end 162 of the groove 150 to prevent further tightening. Similarly, the locking nut 140 and the housing 142 can include, respectively, a first flange 164 and a second flange 166 that meet when the compression seal 114 is fully loosened to prevent the locking nut 140 and the housing 142 from fully separating.

With reference again to FIGS. 1-3, the catheter 102 can include a proximal end portion 168, a distal end portion 170, and a guide-wire lumen 172 having a first guide-wire opening 174 at the proximal end portion 168 and a second guide-wire opening 176 at the distal end portion 170. The guide-wire lumen 172 can extend axially from the first guide-wire opening 174 to the second guide-wire opening 176. The guide-wire lumen 172 can be cylindrical and sized to slidingly receive the guide wire 104. In some embodiments, the catheter 102 includes a guide-wire port 178 toward the proximal end portion 168. Distal to the guide-wire port 178, the catheter 102 can include a hub 180, a balloon seat 182, and a main shaft 184 therebetween. Distal to the main shaft 184, the catheter 102 can include a generally conical tip 186 tapered toward a distal apex 188, and a generally cylindrical sealing portion 190 between the tip 186 and the balloon seat 182. In some embodiments, the second guide-wire opening 176 is at or near the distal apex 188. The tip 186 can be atraumatic. For example, the tip 186 can be configured to dilate one or more blood vessels along a catheterization path generally without injuring the blood vessels. The guide wire 104 can be a J-wire with a diameter of about 0.89 millimeter or have another suitable type and/or size.

The axial length of the catheter 102 from the distal apex 188 to the hub 180 can be from about 50 centimeters to about 100 centimeters, from about 50 centimeters to about 80 centimeters, from about 50 centimeters to about 70 centimeters, or within another suitable range. For example, the axial length of the catheter 102 from the distal apex 188 to the hub 180 can be about 60 centimeters. The axial length of the tip 186 can be from about 3 millimeters to about 30 millimeters, from about 5 millimeters to about 20 millimeters, from about 6 millimeters to about 12 millimeters, or within another suitable range. For example, the axial length of the tip 186 can be about 8 millimeters. The axial length of the sealing portion 190 can be from about 5 millimeters to about 50 millimeters, from about 8 millimeters to about 30 millimeters, from about 10 millimeters to about 20 millimeters, or within another suitable range. For example, the axial length of the sealing portion 190 can be about 14 millimeters.

In some embodiments, the hub 180 includes a first branch 192 axially aligned with the main shaft 184, and a second branch 194 not axially aligned with the main shaft 184, e.g., extending at an angle relative to the main shaft 184. The guide-wire port 178 can be connected to the hub 180 via the first branch 192. The catheter 102 can include an inflation port 196, an inflation valve 198, a second tee fitting 200, a third transition fitting 202, and an inflation conduit 204 connected to the hub 180 via the second branch 194. The inflation valve 198 can include a second thumb turn 205, and can operate similarly to the aspirating valve 136. The hub 180 can include a reinforcing web 206 between the inflation conduit 204 and the guide-wire port 178, and a grip 208 circumferentially positioned generally opposite to the second branch 194. The grip 208 can be configured to be held between a clinician's thumb and index finger, and can include a suitable gripping texture (not shown) on one or both if its major surfaces. Extending laterally from the second tee fitting 200, the catheter 102 can include a pressure-relief valve 210, a fourth transition fitting 212 at one end of the pressure-relief valve 210 toward the second tee fitting 200, and a pressure-relief port 214 at an opposite end of the pressure-relief valve 210.

In some embodiments, the catheter 102 includes a balloon 216 extending around at least a portion of the balloon seat 182, a pair of inflation openings 218 within the balloon 216, and an inflation lumen 220 extending along the main shaft 184 between the inflation port 196 and the inflation openings 218. The catheter 102 can further include a pair of radiopaque bands 221 within the balloon 216 proximate the inflation openings 218. In other embodiments, the catheter 102 can include a different number of inflation openings 218 (e.g. one, three, four, etc.) and/or a different number of radiopaque bands 221 (e.g., zero, one, three, four, etc.). The catheter 102 can further include a rib 222 (FIG. 3) extending along the inflation lumen 220, and a guide-wire tube 224 embedded within the rib 222. The guide-wire lumen 172 can be positioned within the guide-wire tube 224. The pressure-relief valve 210 can be operably connected to the inflation lumen 220 and configured to open when a pressure within the inflation lumen 220 exceeds a threshold pressure. The threshold pressure can be selected to be about equal to a relative pressure within the balloon 216 that is typically necessary to occlude a major blood vessel (e.g., the aorta) or between that relative pressure and a relative pressure within the balloon 216 that typically would burst or otherwise injure the blood vessel. For example, the threshold pressure can be a relative pressure from about 1 atmosphere to about 3 atmospheres, from about 1.5 atmospheres to about 2.5 atmospheres, or within another suitable range. In some embodiments, the threshold pressure is a relative pressure of about 1.9 atmospheres.

Figure 7:
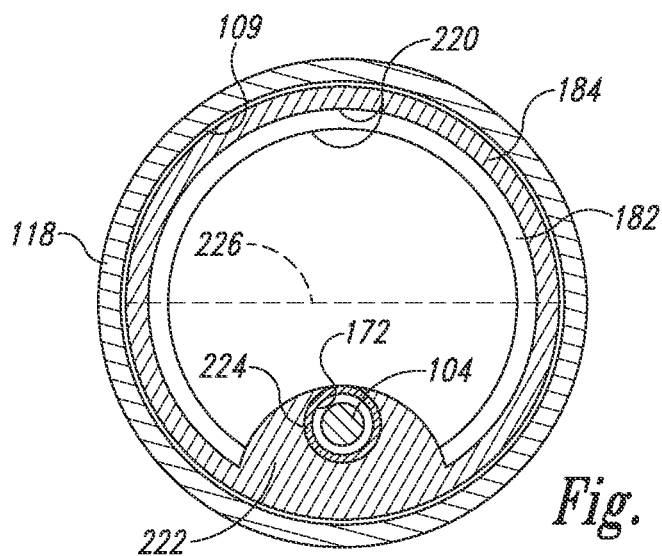
FIGS. 7, 8, and 9 are cross-sectional end views taken, respectively, along lines 7-7, 8-8, and 9-9 in FIG. 5.
Figure 8:
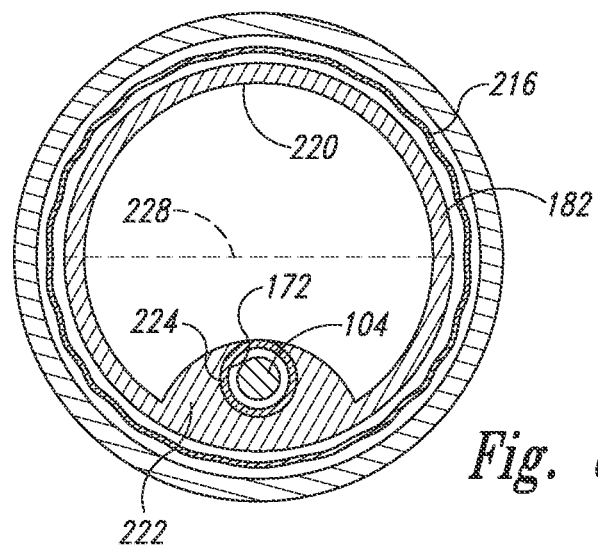
Figure 9:
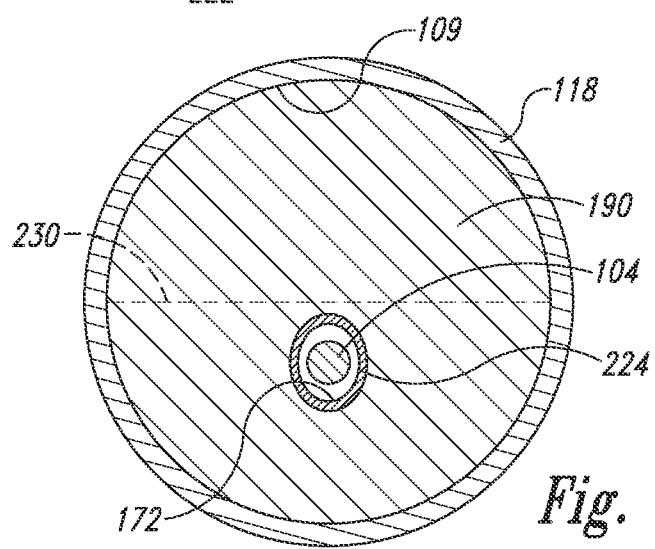

FIG. 5 is a side view illustrating the sheath 100, the catheter 102, and the guide wire 104 in a cooperative arrangement. FIG. 6 is an enlarged view of a portion of FIG. 5. FIGS. 7, 8, and 9 are cross-sectional end views taken, respectively, along lines 7-7, 8-8, and 9-9 in FIG. 5. With reference to FIGS. 5-9 together, in the cooperative arrangement, the sheath 100 can extend around the catheter 102, the catheter 102 can extend around the guide wire 104, and the catheter 102 can be in a delivery state in which the balloon 216 is partially or entirely deflated. The sheath 100 and the catheter 102 can be configured to move together axially relative to the guide wire 104 through blood vessels along a catheterization path. While moving along the catheterization path, the sheath 100 and the catheter 102 can be axially positioned relative to one another with the distal end portion 108 of the sheath 100 around the sealing portion 190 of the catheter 102. The axial length of the sealing portion 190 can be selected to accommodate the distal end portion 108 of the sheath 100 with a suitable tolerance for differential axial movement between the sheath 100 and the catheter 102 while the sheath 100 and the catheter 102 are advanced together along the catheterization path.

The tip 186 can be configured to dilate the blood vessels along the catheterization path ahead of the distal end portion 108. For example, as the sheath 100 and the catheter 102 are advanced together along the catheterization path with the distal end portion 108 around the sealing portion 190, the generally conical shape of the tip 186 can cause the tip 186 to progressively dilate the blood vessels generally evenly around the guide wire 104. The axial length of the tip 186 can be selected to facilitate this process. Furthermore, the tip 186 can include a hydrophilic coating (not shown) on its outer surface that reduces friction between the tip 186 and the blood vessels. The compression seal 114 can be configured to at least partially secure the relative axial positions of the sheath 100 and the catheter 102 while the sheath 100 and the catheter 102 are advanced along the catheterization path. For example, the compression seal 114 can be tightened around the main shaft 184. Furthermore, the main shaft 184 can have a column strength sufficient to resist buckling while the sheath 100 and the catheter 102 are advanced along the catheterization path. In some embodiments, the main shaft 184 has a column strength from about 50% to about 500% of a column strength of the sheath 100. e.g., from about 100% to about 400%, from about 150% to about 300%, or within another suitable range.

The catheter 102 can have different diameters at different portions along its length. For example, the catheter 102 can have a first outer diameter 226 (FIG. 7) at the main shaft 184, a second outer diameter 228 (FIG. 8) at the balloon seat 182, and a third outer diameter 230 (FIG. 9) between the tip 186 and the balloon seat 182, e.g., at the sealing portion 190. The second outer diameter 228 can be less than the first outer diameter 226, and/or the third diameter 230 can be about equal to or greater than the first outer diameter 226. The third outer diameter 230 can be selected to cause a snug fit between the sealing portion 190 and the sheath 100, e.g., at the distal end portion 108. The first outer diameter 226 can be selected to reduce friction between the sheath 100 and the main shaft 184, such that the friction between the sheath 100 and the main shaft 184 is less than the friction between the sheath 100 and the sealing portion 190. The second outer diameter 228 can be selected to provide sufficient space between the balloon seat 182 and the sheath 100 to accommodate the balloon 216 when the balloon 216 is not inflated. The cross-sectional area of the rib 222 can increase or decrease along the length of the catheter 102, e.g., in conjunction with changes in the diameter of the catheter 102. For example, the rib 222 can have a smaller cross-sectional area along the balloon seat 182 than along the main shaft 184. Distal to the rib 222, the guide-wire tube 224 can angle toward the central axis of the catheter 102 so as to align with the second guide-wire opening 176.

The snug fit between the distal end portion 108 and the sealing portion 190, alone or in combination with the tapered shape of the distal end portion 108, can cause a distal interface between the sheath 100 and the catheter 102 to be generally atraumatic. For example, the size and shape of the distal end portion 108 can reduce or prevent vascular injury from a corner or edge of the sheath 100 scraping or gouging inside surfaces of blood-vessel walls along the catheterization path. In some embodiments, the catheter 102 has greater compressibility at the sealing portion 190 than at the balloon seat 182 and/or at the main shaft 184. This can be useful, for example, to facilitate the snug fit between the sealing portion 190 and the sheath 100 and/or to increase friction between the sealing portion 190 and the sheath 100. In some embodiments, the catheter 102 has a compressibility at the sealing portion 190 from about 20% to about 800% greater than at the balloon seat 182, e.g., from about 50% to about 500%, from about 100% to about 300%, or within another suitable range.

With reference to FIG. 9, the catheter 102 can have a generally solid cross-sectional area around the guide-wire tube 224 at the sealing portion 190. In other embodiments, the sealing portion 190 can be at least partially hollow. The sealing portion 190 can have a different composition than the composition of the balloon seat 182 and/or the composition of the main shaft 184. For example, the sealing portion 190 can be made of a material that is softer than a material of the balloon seat 182 and/or of the main shaft 184. In some embodiments, the sealing portion 190 is made of rubber or a similar material while the balloon seat 182 and the main shaft 184 are made of polyimide or a similar material. In other embodiments, the sealing portion 190, the balloon seat 182, and the main shaft 184 can have other suitable compositions.

Before use, the inflation lumen 220 and the balloon 216 can be purged of air while the catheter 102 is outside of the sheath 100. This process can include attaching a syringe (not shown) to the inflation port 196, opening the inflation valve 198, and pressing a plunger of the syringe to introduce a suitable liquid (e.g., saline) into the balloon 216. The syringe can then be removed and the catheter 102 can be reoriented, if necessary, so that the inflation port 196 is above other portions of the catheter 102. The balloon 216 can then be squeezed to displace the remaining air until the fluid exits the inflation port 196. The syringe can then be reconnected to the inflation port 196 and used to withdraw additional fluid until the balloon 216 is fully deflated. Toward the end of this operation, the second thumb turn 205 can be used to close the inflation valve 198 to retain the liquid within the inflation lumen 220 and the balloon 216 and to prevent air from entering the inflation lumen 220 and the balloon 216. After the air has been purged, the sheath 100 and the catheter 102 can be suitably positioned relative to one another in the cooperative arrangement and the compression seal 114 can be tightened around the main shaft 184.

The preparation steps, e.g., purging air from the inflation lumen 220 and the balloon 216 and axially positioning the sheath 100 and the catheter 102 relative to one another, can be time consuming. In some embodiments, these operations can be performed in advance of use. For example, the catheter 102 and the sheath 100 can be positioned within a sealed package (not shown) in a generally sterile condition. Within the package, the inflation lumen 220 and the balloon 216 can contain a suitable fluid, e.g., with generally all air purged from the inflation lumen 220 and the balloon 216. Furthermore, the sheath 100 and the catheter 102 can be pre-positioned relative to one another with the distal end portion 108 of the sheath 100 around the sealing portion 190 of the catheter 102, and the compression seal 114 can be tightened around the main shaft 184. The sheath 100 and the catheter 102 can be disposable. Thus, in some embodiments, a clinician can simply open the package and deploy the sheath 100 over the guide wire 104 with few, if any, intervening operations. In other embodiments, the sheath 100 and the catheter 102 can be reusable. Furthermore, in some embodiments, the catheter 102 can be configured to be purged of air and/or the catheter 102 and the sheath 100 can be configured to be axially positioned relative to one another after being removed from the package.

Figure 10:
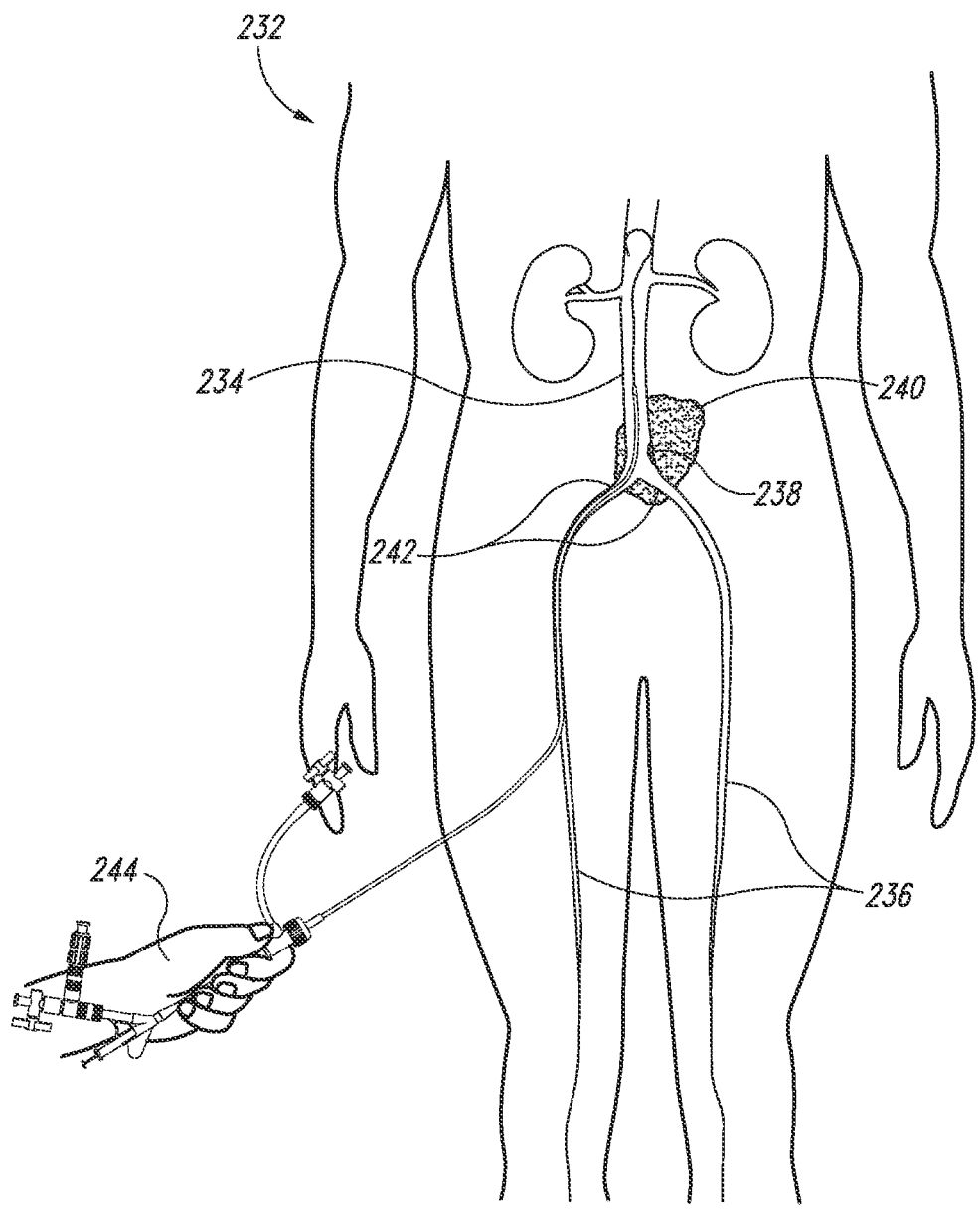
FIG. 10 is a partially cross-sectional anatomical front view illustrating advancing the sheath and the catheter shown in FIG. 1 along the guide wire shown in FIG. 1 during aortic occlusion in accordance with an embodiment of the present technology.

FIG. 10 is a partially cross-sectional anatomical front view illustrating advancing the sheath 100 and the catheter 102 along the guide wire 104 during a method for aortic occlusion in accordance with an embodiment of the present technology. The guide wire 104 can be introduced into the vasculature of a patient 232 using conventional techniques. For example, the guide wire 104 can be extended into the aorta 234 via a catheterization path including a femoral artery 236. In other embodiments, another suitable catheterization path can be used, e.g., a catheterization path including a radial artery. In the illustrated embodiment, the patient 232 has a vascular injury 238 causing a hematoma 240 in the region of the external iliac arteries 242. A clinician 244 can simultaneously advance the catheter 102 and the sheath 100 along the catheterization path while the tip 186 of the catheter 102 dilates the blood vessels along the catheterization path. While the catheter 102 and the sheath 100 are simultaneously advanced, the compression seal 114 (not shown in FIG. 10) of the sheath 100 can be tightened around the catheter 102. In some embodiments, the axial length of the catheter 102 can be from about 100% to about 150% of the length of the catheterization path, e.g., from about 110% to about 130%, or within another suitable range. Excess length of the catheter 102 can be undesirable in some cases, because it can reduce the column strength of the catheter 102 and/or cause the catheter 102 to be more cumbersome to operate.

Figure 11:
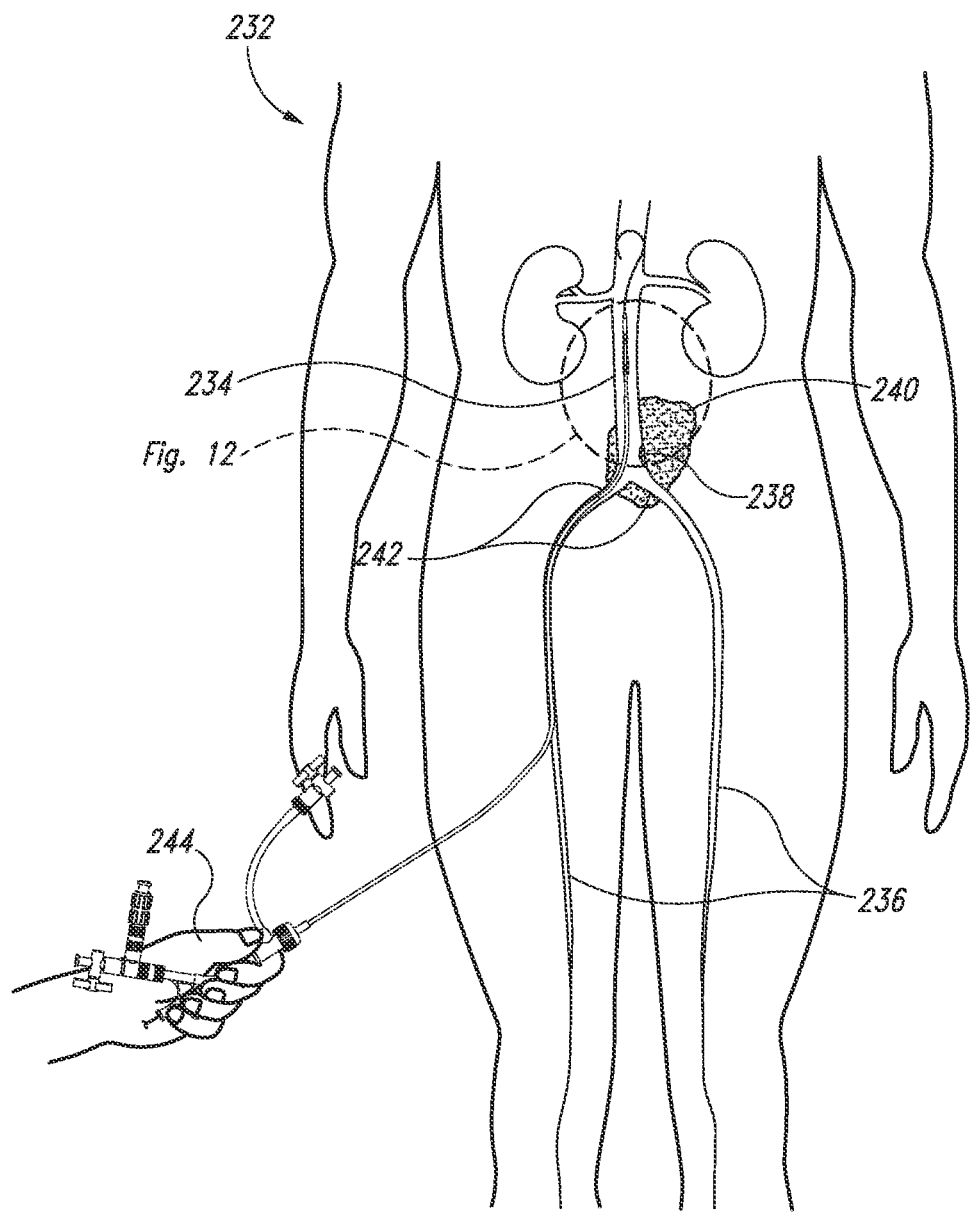
FIG. 11 is a partially cross-sectional anatomical front view illustrating exposing the balloon of the catheter shown in FIG. 1 during aortic occlusion in accordance with an embodiment of the present technology.

FIG. 11 is a partially cross-sectional anatomical front view illustrating exposing the balloon 216. After the clinician 244 simultaneously advances the sheath 100 and the catheter 102, the clinician 244 can loosen the compression seal 114 and then move the sheath 100 and/or the catheter 102 relative to one another to cause the balloon 216 to extend beyond the distal end portion 108 of the sheath 100. For example, the catheter 102 can be advanced relative to the sheath 100 and/or the sheath 100 can be retracted relative to the catheter 102. In some embodiments, the balloon 216 can be positioned upstream from the vascular injury 238 while, immediately before, or immediately after exposing the balloon 216. In other embodiments, the balloon 216 can be positioned at another suitable location and/or at another suitable time. The sheath 100 can be configured to hold the catheter 102 at all times during use. In some cases, the sheath 100 is not configured to hold open blood vessels along the catheterization path without the presence of the catheter 102. The sheath 100, for example, can be unreinforced along at least about 50%, e.g., at least about 75% or generally all of its axial length. In other embodiments, the sheath 100 can be fully reinforced and/or can have a resistance to collapsing from compression or other lateral forces similar to that of conventional sheaths configured for use with removable dilators.

When the balloon 216 is exposed, the distal end portion 108 of the sheath 100 can be positioned around a portion of the balloon seat 182 proximal to the balloon 216. In other embodiments, when the balloon 216 is exposed, the distal end portion 108 of the sheath 100 can be positioned around the main shaft 184. An annular space between the catheter 102 and the sheath 100 (e.g., between the main shaft 184 and the sheath 100 and, in some cases, between the portion of the balloon seat 182 proximal to the balloon 216 and the sheath 100) can be open to the aorta 234. Thus, the sheath 100 can serve as an arterial line accessible via the valve assembly 126. The inner diameter of the central lumen 109 of the sheath 100, the first outer diameter 226 of the catheter 102 at the main shaft 184, and, in some cases, the second outer diameter 228 of the catheter at the balloon seat 182 can be selected to facilitate this function. In some embodiments, a suitably calibrated blood-pressure monitor (not shown) can be connected to the aspirating port 132, and the aspirating valve 136 can be opened to provide a fluidic connection between the blood-pressure monitor and the aorta 234. In this way, the aortic blood pressure can be monitored directly, providing the clinician 244 with useful near-real-time information concerning the status of the patient 232. Furthermore, both before and after the balloon 216 is inflated, blood can be aspirated via the annular space and/or drugs, saline, and/or other suitable substances can be introduced into the aorta 234 via the annular space.

Figure 12:
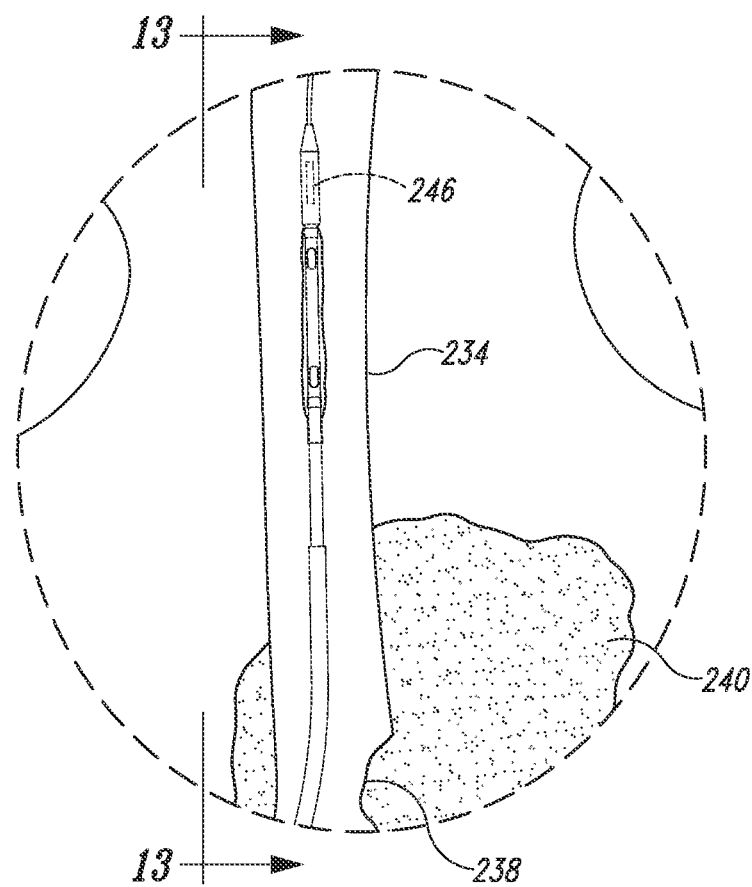
FIG. 12 is an enlarged view of a portion of FIG. 11.
Figure 13:
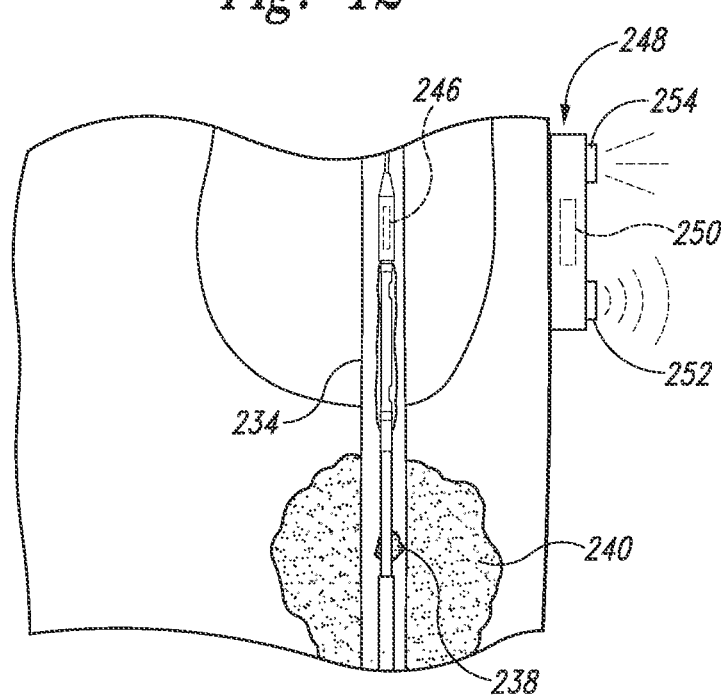
FIG. 13 is a partially cross-sectional anatomical side view taken along line 13-13 in FIG. 12 further illustrating using an extracorporeal proximity sensor to position the balloon of the catheter shown in FIG. 1 upstream from a vascular injury.

FIG. 12 is an enlarged view of a portion of FIG. 11. FIG. 13 is a partially cross-sectional anatomical side view taken along line 13-13 in FIG. 12. With reference to FIGS. 12 and 13 together, the catheter 102 can include a proximity-sensor target 246 embedded within the sealing portion 190. In other embodiments, the proximity-sensor target 246 can be positioned at another suitable portion of the catheter 102 or the sheath 100. In some cases, the proximity-sensor target 246 is positioned less than about 10 centimeters from the balloon seat 182 and/or from the balloon 216. The proximity-sensor target 246 alone or together with the radiopaque bands 221 can be used to position the catheter 102 and/or the sheath 100 within the aorta 234. For example, the proximity-sensor target 246 can facilitate proximity-based positioning and the radiopaque bands 221 can facilitate fluoroscopic positioning. In some embodiments, proximity-based positioning can be well-suited for providing approximate positioning information to the clinician 244 when more precise fluoroscopic positioning is not available, e.g. outside of a hospital operating room or trauma center. In many cases, the high precision of fluoroscopic positioning is not necessary and/or desirable. For example, it can be sufficient to merely confirm that the balloon 216 is upstream from the location of the vascular injury 238 and/or to approximately track insertion of the catheter 102 before inflating the balloon 216. The approximate location of the vascular injury 238 is often apparent, e.g., based on the location of a gunshot wound or visible swelling associated with a ruptured aneurysm.

The catheter 102 can be part of a system further including an extracorporeal proximity sensor 248 (FIG. 13) configured to locate the proximity-sensor target 246. FIG. 13 illustrates using the proximity sensor 248 to position the balloon 216 upstream from the vascular injury 238. For example, the proximity sensor 248 can be used to determine a position of the proximity-sensor target 246, and that position can be correlated to a position of the balloon 216. In some embodiments, the proximity sensor 248 includes a detector 250 configured to receive a signal (e.g., including multiple individual signals) from the proximity-sensor target 246. For example, the proximity-sensor target 246 can include a passive radiofrequency tag (not shown) and the proximity sensor 248 can be configured to energize the tag to generate the signal. In other embodiments, the proximity sensor 248 can be configured to locate the proximity-sensor target 246 without the signal. For example, the proximity-sensor target 246 can be a metal slug and the proximity sensor 248 can include a magnetic sensor. In still other embodiments, the proximity sensor 248 can include a capacitance sensor, a short-range impulse radar sensor, or another suitable proximity sensing component.

Determining the position of the proximity-sensor target 246 can include moving the proximity sensor 248 relative to the patient 232 until the proximity sensor 248 indicates an external location on the patient 232 corresponding to the position of the proximity-sensor target 246. For example, the clinician 244 can perform a first sweep during which the proximity sensor 248 is moved over a portion of the patient 232 approximately corresponding to the position of the proximity-sensor target 246 while the proximity sensor 248 is in a first or scanning mode, and then perform a second sweep during which the proximity sensor 248 is moved over the portion of the patient 232 again while the proximity sensor 248 is in a second or detecting mode. Based on data (e.g., proximity measurements) collected by the proximity sensor 248 during the first sweep, the proximity sensor 248 can identify a location at which the proximity sensor 248 is closest to the proximity-sensor target 246 during the second sweep. The proximity sensor 248 can include an audible alarm 252 and/or a visual alarm 254 configured to alert the clinician 244 when the proximity sensor 248 is closest to the proximity-sensor target 246 during the second sweep. In other embodiments, the proximity sensor 248 can have a single operational mode. For example, the audible alarm 252 can be variable (e.g. in volume, pitch, frequency, etc.) and/or the visual alarm 254 can be variable (e.g., in brightness, color, etc.) to indicate a relative proximity of the proximity sensor 248 to the proximity-sensor target 246. The clinician 244 can use variation in the audible alarm 252 and/or the visual alarm 254 to guide the proximity sensor 248 toward the location at which the proximity sensor 248 is closest to the proximity-sensor target 246.

Figure 14:
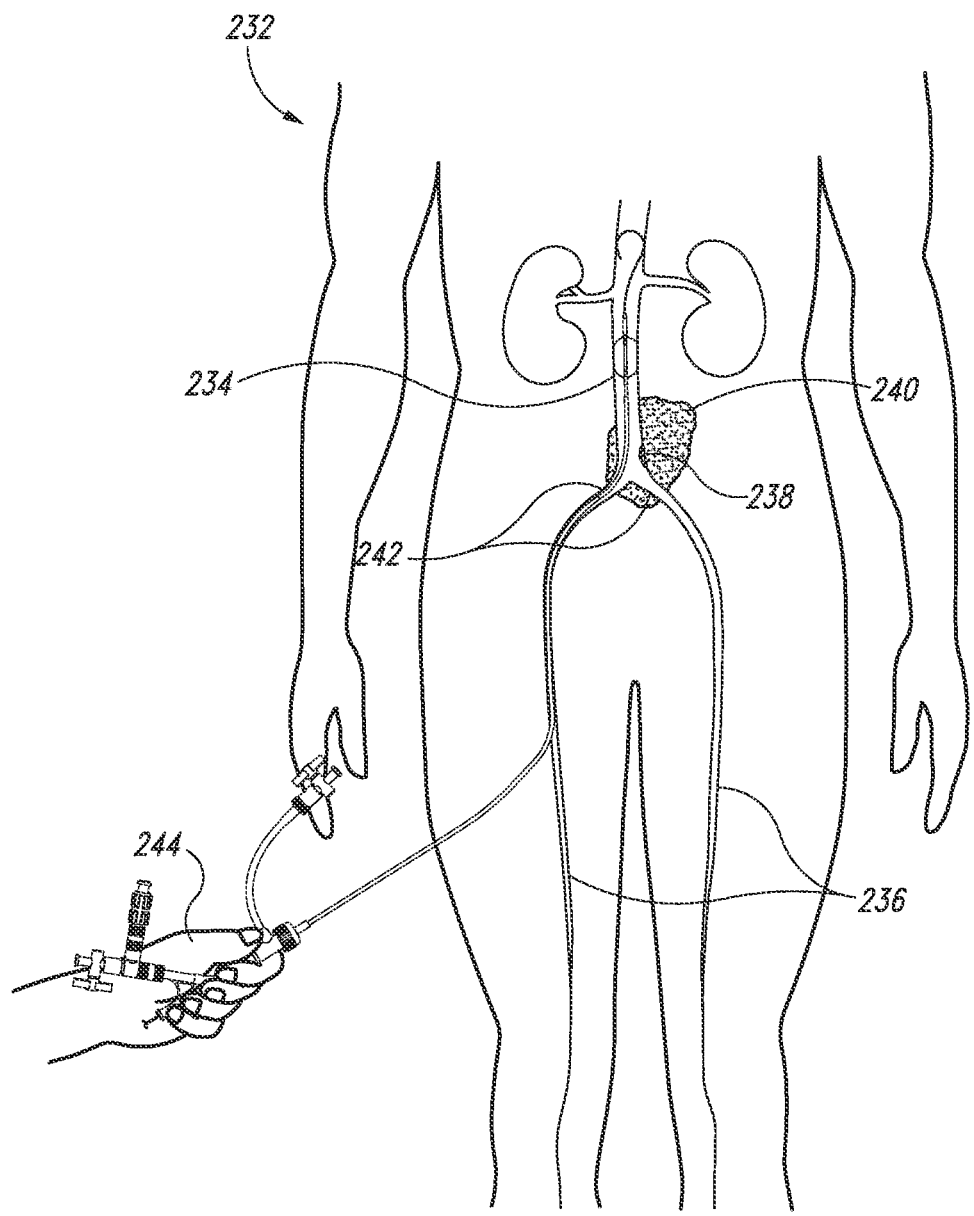
FIG. 14 is a partially cross-sectional anatomical front view illustrating inflating the balloon of the catheter shown in FIG. 1 during aortic occlusion in accordance with an embodiment of the present technology.

FIG. 14 is a partially cross-sectional anatomical front view illustrating inflating the balloon 216 to at least partially occlude the aorta 234 after exposing the balloon 216. Inflating the balloon 216 can include attaching a syringe (not shown) to the inflation port 196, opening the inflation valve 198, and pressing a plunger of the syringe to introduce a suitable liquid (e.g., saline) into the balloon 216 until the pressure-relief valve 210 opens. After the balloon 216 has been inflated, the inflation valve 198 can be removed and the vascular injury 238 can be repaired, e.g., by introducing an endoprosthesis or by performing limited open surgery. The balloon 216 can then be deflated by reopening the inflation valve 198 and pulling the plunger of the syringe to draw the fluid out of the balloon 216. The catheter 102 and/or the sheath 100 can then be moved relative to one another to position the distal end portion 108 of the sheath 100 around the sealing portion 190 of the catheter 102 before simultaneously withdrawing the catheter 102 and the sheath 100 from the vasculature of the patient 232.

EXAMPLES

1. A catheter, comprising:
a tapered tip including a distal apex;
a guide-wire opening at or near the distal apex;
a balloon seat proximal to the tip;
a balloon extending around at least a portion of the balloon seat;
an inflation opening positioned within the balloon;
a main shaft proximal to the balloon seat;
a hub proximal to the main shaft;
an inflation port proximal to the hub; and
an inflation lumen extending along the main shaft between the inflation port and the inflation opening, wherein—
the catheter has a first outer diameter at the main shaft, a second outer diameter at the balloon seat, and a third outer diameter between the tip and the balloon seat,
the second outer diameter is less than the first outer diameter, and
the third outer diameter is about equal to or greater than the first outer diameter.

2. The catheter of example 1 wherein an axial length of the catheter between the hub and the distal apex is from about 50 centimeters to about 100 centimeters.

3. The catheter of example 1 wherein an axial length of the tip is from about 3 millimeters to about 30 millimeters.

4. The catheter of example 1, further comprising a proximity-sensor target positioned less than about 10 centimeters from the balloon seat.

5. The catheter of example 1, further comprising a sealing portion between the tip and the balloon, the sealing portion having an axial length from about 5 millimeters to about 50 millimeters.

6. The catheter of example 5 wherein a compressibility of the catheter at the sealing portion is greater than a compressibility of the catheter at the balloon seat, a compressibility of the catheter at the main shaft, or both.

7. The catheter of example 1, further comprising a pressure-relief valve operably connected to the inflation lumen.

8. The catheter of example 7 wherein:
the catheter is configured to occlude a major blood vessel; and
the pressure-relief valve is configured to open at a threshold pressure between a relative pressure within the balloon necessary to occlude the blood vessel and a relative pressure within the balloon that would burst or otherwise injure the blood vessel.

9. The catheter of example 7, further comprising:
a guide-wire port connected to the hub via a first branch of the hub;
a guide-wire lumen extending along the main shaft between the guide-wire port and the guide-wire opening; and
an inflation valve between the inflation port and the hub, wherein—
the inflation port, the inflation valve, and the pressure-relief valve are connected to the hub via a second branch of the hub,
the first branch is axially aligned with the main shaft, and
the second branch is not axially aligned with the main shaft.

10. A catheter system, comprising:
a catheter including—
an atraumatic tip,
a sealing portion proximal to the tip, the sealing portion having an axial length from about 5 millimeters to about 50 millimeters,
a balloon proximal to the sealing portion,
an inflation opening positioned within the balloon,
a main shaft proximal to the balloon,
an inflation port proximal to the main shaft, and
an inflation lumen extending along the main shaft between the inflation port and the inflation opening; and
a sheath including a tapered distal end portion configured to fit snugly around the sealing portion, wherein the tip is configured to dilate one or more blood vessels along a catheterization path ahead of the distal end portion as the catheter and the sheath are advanced together along the catheterization path with the distal end portion around the scaling portion.

11. The system of example 10 wherein the main shaft has a column strength sufficient to resist buckling as the catheter and the sheath are advanced together along the catheterization path.

12. The system of example 10 wherein the main shaft has a column strength from about 100% to about 400% of a column strength of the sheath.

13. The system of example 10 wherein the sheath is unreinforced along at least about 50% of its axial length.

14. The system of example 10 wherein:
the tip has a generally conical shape with a distal apex;
the tip has an axial length from about 3 millimeters to about 30 millimeters; and
the catheter further includes a guide-wire opening at or near the distal apex.

15. The system of example 10 wherein the sheath further includes an adjustable compression seal configured to be tightened around the main shaft.

16. The system of example 10, further comprising an extracorporeal proximity sensor, wherein:
the catheter further includes a proximity-sensor target less than about 10 centimeters from the balloon; and
the proximity sensor is configured to locate the proximity-sensor target.

17. The system of example 10 wherein:
the sheath further includes a valve assembly; and
an inner diameter of the sheath and an outer diameter of the main shaft are selected to facilitate use of the sheath as an arterial line.

18. The system of example 10, further comprising a sealed package, wherein:
the catheter and the sheath are generally sterile and positioned within the package;
the catheter is axially positioned within the sheath with the distal end portion around the sealing portion; and
the balloon and the inflation lumen contain a liquid.

19. The system of example 18 wherein the sheath further includes an adjustable compression seal tightened around the main shaft.

20. A method for occluding an injured blood vessel, comprising:
simultaneously advancing a catheter and a sheath along a catheterization path while a tip of the catheter dilates one or more blood vessels along the catheterization path;
advancing the catheter and/or retracting the sheath to cause a balloon of the catheter to extend beyond a distal end portion of the sheath after simultaneously advancing the catheter and the sheath along the catheterization path; and
inflating the balloon to at least partially occlude the injured blood vessel.

21. The method of example 20, further comprising selecting an axial length of the catheter to be from about 100% to about 150% of the length of the catheterization path.

22. The method of example 20, further comprising monitoring blood pressure within the injured blood vessel via an annular space between the catheter and the sheath before inflating the balloon and after advancing the catheter and/or retracting the sheath to cause the balloon of the catheter to extend beyond the distal end portion of the sheath.

23. The method of example 20 wherein:
simultaneously advancing the catheter and the sheath along the catheterization path includes simultaneously advancing the catheter and the sheath while an adjustable compression seal of the sheath is tightened around the catheter; and
the method further comprises loosening the adjustable compression seal before advancing the catheter and/or retracting the sheath to cause the balloon to extend beyond the distal end portion.

24. The method of example 20, further comprising using the sheath as an arterial line after advancing the catheter and/or retracting the sheath to cause the balloon of the catheter to extend beyond the distal end portion of the sheath.

25. The method of example 24 wherein using the sheath as an arterial line includes measuring a blood pressure within the injured blood vessel via an annular space between the catheter and the sheath.

26. The method of example 20, further comprising determining a position of a proximity-sensor target of the catheter or the sheath using an extracorporeal proximity sensor after simultaneously advancing the catheter and the sheath along the catheterization path.

27. The method of example 26, further comprising confirming that the balloon is upstream from a location of a vascular injury by determining the position of the proximity-sensor target.

28. The method of example 26 wherein the proximity-sensor target includes a passive radiofrequency tag and determining the position of the proximity-sensor target includes energizing the tag using the proximity sensor.

29. The method of example 26 wherein determining the position of the proximity-sensor target includes moving the proximity sensor relative to a patient until the proximity sensor indicates an external location on the patient corresponding to the position of the proximity-sensor target.

Closing

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. While advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown or described herein.

Certain aspects of the present technology may take the form of computer-executable instructions, including routines executed by a controller or other data processor. In some embodiments, a controller or other data processor can be specifically programmed, configured, or constructed to perform one or more of these computer-executable instructions. Furthermore, some aspects of the present technology may take the form of data. e.g., non-transitory data, stored or distributed on computer-readable media, including magnetic or optically readable or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout to mean including at least the recited feature(s) such that any greater number of the same feature and/or additional types of other features are not precluded. Directional terms, such as "upper," "lower." "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. A catheter sized and shaped for delivery to a major blood vessel of a human patient, the catheter comprising:
    a tapered tip including a distal apex;
    a guide-wire opening at or near the distal apex;
    a balloon seat proximal to the tip;
    a balloon extending around at least a portion of the balloon seat;
    an inflation opening positioned within the balloon;
    a main shaft proximal to the balloon seat having a column strength from about 50% to about 500% of a column strength of a sheath encompassing at least a portion of the main shaft;
    a hub proximal to the main shaft;
    an inflation port proximal to the hub;
    an inflation lumen extending along the main shaft between the inflation port and the inflation opening; and
    a pressure-relief valve operably connected to the inflation lumen,
    wherein, during operation, the catheter is configured to occlude the major blood vessel, and wherein the pressure-relief valve is configured to open at a threshold pressure between a relative pressure within the balloon necessary to occlude the blood vessel and a relative pressure within the balloon that would burst or otherwise injure the blood vessel,
    wherein—
        the catheter has a first outer diameter at the main shaft, a second outer diameter at the balloon seat, and a third outer diameter between the tip and the balloon seat,
        the second outer diameter is less than the first outer diameter, and
        the third outer diameter is about equal to or greater than the first outer diameter.

2. The catheter of claim 1 wherein an axial length of the catheter between the hub and the distal apex is from about 50 centimeters to about 100 centimeters.

3. The catheter of claim 1 wherein an axial length of the tip is from about 3 millimeters to about 30 millimeters.

4. The catheter of claim 1, further comprising a proximity-sensor target positioned less than about 10 centimeters from the balloon seat.

5. The catheter of claim 1, further comprising a sealing portion between the tip and the balloon, the sealing portion having an axial length from about 5 millimeters to about 50 millimeters.

6. The catheter of claim 5 wherein a compressibility of the catheter at the sealing portion is greater than a compressibility of the catheter at the balloon seat, a compressibility of the catheter at the main shaft, or both.

7. The catheter of claim 1, further comprising:
    a guide-wire port connected to the hub via a first branch of the hub;
    a guide-wire lumen extending along the main shaft between the guide-wire port and the guide-wire opening; and
    an inflation valve between the inflation port and the hub, wherein—
        the inflation port, the inflation valve, and the pressure-relief valve are connected to the hub via a second branch of the hub,
        the first branch is axially aligned with the main shaft, and
        the second branch is not axially aligned with the main shaft.

8. A catheter system, comprising:
    a catheter including—
        an atraumatic tip,
        a sealing portion proximal to the tip, the sealing portion having an axial length from about 5 millimeters to about 50 millimeters,
        a balloon proximal to the sealing portion,
        an inflation opening positioned within the balloon,
        a main shaft proximal to the balloon,
        an inflation port proximal to the main shaft, and
        an inflation lumen extending along the main shaft between the inflation port and the inflation opening,
        wherein, when inflated, the balloon is sized and shaped to occlude a major blood vessel of a human patient; and
    a sheath including a tapered distal end portion configured to fit snugly around the sealing portion,
    wherein the tip is configured to dilate one or more blood vessels along a catheterization path ahead of the distal end portion as the catheter and the sheath are advanced together along the catheterization path with the distal end portion around the sealing portion, and wherein the main shaft has a column strength from about 50% to about 500% of a column strength of the sheath.

9. The system of claim 8 wherein the main shaft has a column strength sufficient to resist buckling as the catheter and the sheath are advanced together along the catheterization path.

10. The system of claim 8 wherein the column strength is from about 100% to about 400% of the column strength of the sheath.

11. The system of claim 8 wherein the sheath is unreinforced along at least about 50% of its axial length.

12. The system of claim 8 wherein:

the tip has a generally conical shape with a distal apex;

the tip has an axial length from about 3 millimeters to about 30 millimeters; and the catheter further includes a guide-wire opening at or near the distal apex.

13. The system of claim 8 wherein the sheath further includes an adjustable compression seal configured to be tightened around the main shaft.

14. The system of claim 8, further comprising an extracorporeal proximity sensor, wherein:

the catheter further includes a proximity-sensor target less than about 10 centimeters from the balloon; and the proximity sensor is configured to locate the proximity-sensor target.

15. The system of claim 8 wherein:

the sheath further includes a valve assembly; and an inner diameter of the sheath and an outer diameter of the main shaft are selected to facilitate use of the sheath as an arterial line.

16. The system of claim 8, further comprising a sealed package, wherein:

the catheter and the sheath are generally sterile and positioned within the package;

the catheter is axially positioned within the sheath with the distal end portion around the sealing portion; and the balloon and the inflation lumen contain a liquid.

17. The system of claim 16 wherein the sheath further includes an adjustable compression seal tightened around the main shaft.

18. The catheter of claim 1 wherein the column strength is from about 100% to about 400% of the column strength of the sheath.

* * * * *